United States Patent
Ruppertshofen et al.

(10) Patent No.: US 9,839,404 B2
(45) Date of Patent: Dec. 12, 2017

(54) IMAGE DATA Z-AXIS COVERAGE EXTENSION FOR TISSUE DOSE ESTIMATION

(71) Applicant: KONINKLIJKE PHILIPS N.V., Eindhoven (NL)

(72) Inventors: Heike Ruppertshofen, Hamburg (DE); Cristian Lorenz, Hamburg (DE); Jens Wiegert, Aachen (DE); Peter Prinsen, Eindhoven (NL); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 73 days.

(21) Appl. No.: 14/916,592

(22) PCT Filed: Sep. 11, 2014

(86) PCT No.: PCT/IB2014/064425
§ 371 (c)(1),
(2) Date: Mar. 4, 2016

(87) PCT Pub. No.: WO2015/044817
PCT Pub. Date: Apr. 2, 2015

(65) Prior Publication Data
US 2016/0206263 A1    Jul. 21, 2016

Related U.S. Application Data

(60) Provisional application No. 61/883,566, filed on Sep. 27, 2013.

(51) Int. Cl.
*A61B 6/00* (2006.01)
*A61B 6/14* (2006.01)
(Continued)

(52) U.S. Cl.
CPC ........... *A61B 6/488* (2013.01); *A61B 6/032* (2013.01); *A61B 6/10* (2013.01); *A61B 6/14* (2013.01);
(Continued)

(58) Field of Classification Search
None
See application file for complete search history.

(56) References Cited

U.S. PATENT DOCUMENTS 6,148,272 A    11/2000   Bergstrom
7,787,669 B2    8/2010   Botterweck
(Continued)

FOREIGN PATENT DOCUMENTS

WO         98/47085      10/1998
WO       2007/062178      5/2007
(Continued)

OTHER PUBLICATIONS

Wiegert et al. "Projection Extension for Region of Interest Imaging in Cone-Beam CT," Acad Radiol 2005; 12:1010-1023.*
(Continued)

*Primary Examiner* — Matthew Bella
*Assistant Examiner* — Soo Shin

(57) ABSTRACT

A method for extending initial image data of a subject for dose estimation includes obtaining first image data of the subject for dose calculation, wherein the first image data has a first field of view. The method further includes obtaining second image data for extending the field of view of the first image data. The second image data has a second field of view that is larger than the first field of view. The method further includes extending the first field of view based on the second image data, producing extended image data.

17 Claims, 5 Drawing Sheets

(51) Int. Cl.
  *A61C 9/00* (2006.01)
  *A61B 6/03* (2006.01)
  *A61B 6/10* (2006.01)
  *A61N 5/10* (2006.01)
  *G06T 19/00* (2011.01)
  *G06F 19/00* (2011.01)
  *G06T 7/174* (2017.01)
  *G06T 7/30* (2017.01)

(52) U.S. Cl.
  CPC .......... *A61B 6/5229* (2013.01); *A61B 6/5235* (2013.01); *A61B 6/542* (2013.01); *A61C 9/006* (2013.01); *A61C 9/0046* (2013.01); *A61C 9/0053* (2013.01); *A61C 9/0086* (2013.01); *G06F 19/321* (2013.01); *G06T 7/174* (2017.01); *G06T 7/30* (2017.01); *G06T 19/006* (2013.01); *A61B 6/5247* (2013.01); *A61N 5/1031* (2013.01); *G06T 2207/10081* (2013.01); *G06T 2207/20221* (2013.01); *G06T 2210/41* (2013.01)

(56) References Cited

U.S. PATENT DOCUMENTS

| | | |
|---|---|---|
| 2007/0038058 A1 | 2/2007 | West |
| 2007/0041495 A1* | 2/2007 | Olivera .................. A61N 5/103 378/65 |
| 2007/0116344 A1* | 5/2007 | Hsieh ..................... A61B 6/032 382/131 |
| 2007/0147579 A1 | 6/2007 | De Man |
| 2008/0159611 A1 | 7/2008 | Tao et al. |
| 2008/0292055 A1* | 11/2008 | Boone ....................... G01T 1/02 378/97 |
| 2009/0097722 A1* | 4/2009 | Dekel ..................... G06T 15/10 382/128 |
| 2010/0046696 A1 | 2/2010 | Maltz |
| 2010/0208964 A1* | 8/2010 | Wiegert ................. G06T 11/005 382/131 |
| 2011/0080168 A1* | 4/2011 | Fenchel ................. A61B 6/037 324/309 |
| 2012/0128116 A1 | 5/2012 | Sabol |
| 2012/0148132 A1 | 6/2012 | Couch |
| 2012/0230470 A1 | 9/2012 | Bertram |
| 2013/0177224 A1 | 7/2013 | Papageorgiou |
| 2013/0190590 A1 | 7/2013 | Kadir |
| 2015/0003709 A1 | 1/2015 | Boemert |
| 2015/0371420 A1* | 12/2015 | Yerushalmy .......... G06T 3/4038 382/284 |

FOREIGN PATENT DOCUMENTS

| | | |
|---|---|---|
| WO | 2009/004523 | 1/2009 |
| WO | 2015/087185 | 6/2015 |

OTHER PUBLICATIONS

Pace et al. "Deformable Image Registration of Sliding Organs Using Anisotropic Diffusive Regularization," Proc IEEE Int Symp Biomed Imaging. Mar. 30, 2011; : 407-413.*

Maes et al. "Medical Image Registration Using Mutual Information," Poceedings of the IEEE, vol. 91, No. 10, Oct. 2003.*

Kabus, "Multiple-Material Variational Image Registration", PhD thesis, Universitat zu Lubeck, 2006.

Parham Alaei, "Calculating Organ Dose from Fluoroscopy", 2011.

* cited by examiner

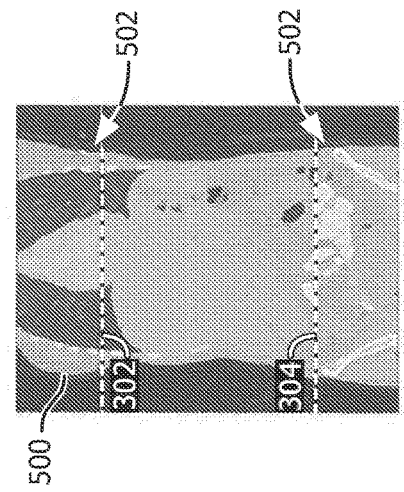 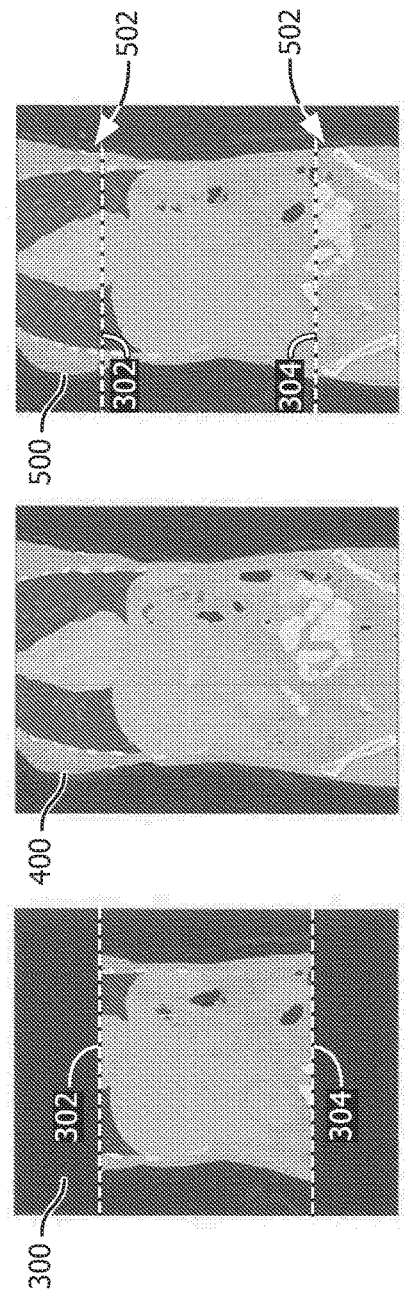 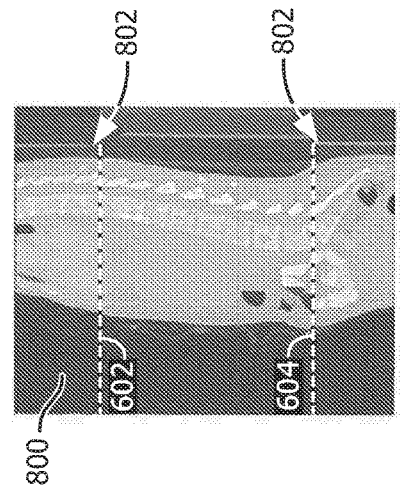 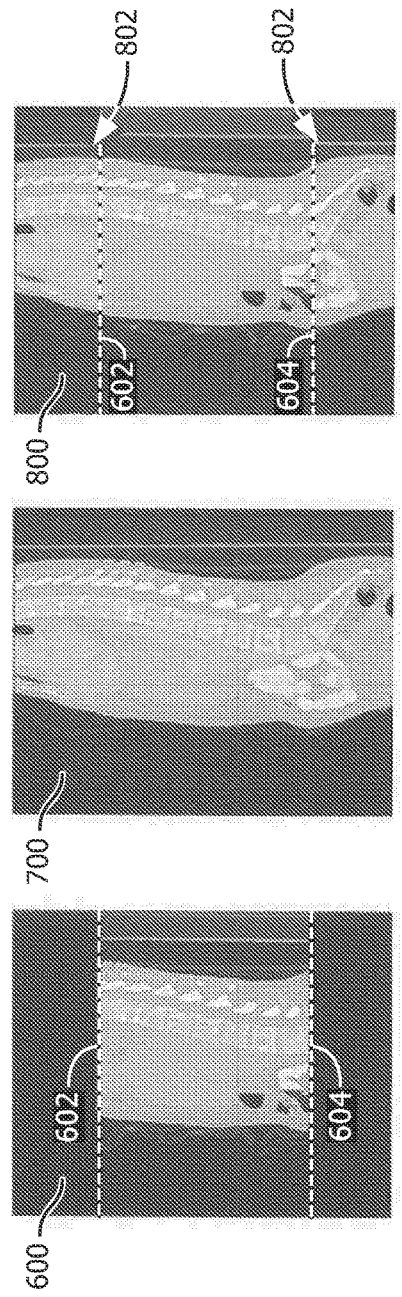
FIG. 3　FIG. 4　FIG. 5　FIG. 6　FIG. 7　FIG. 8

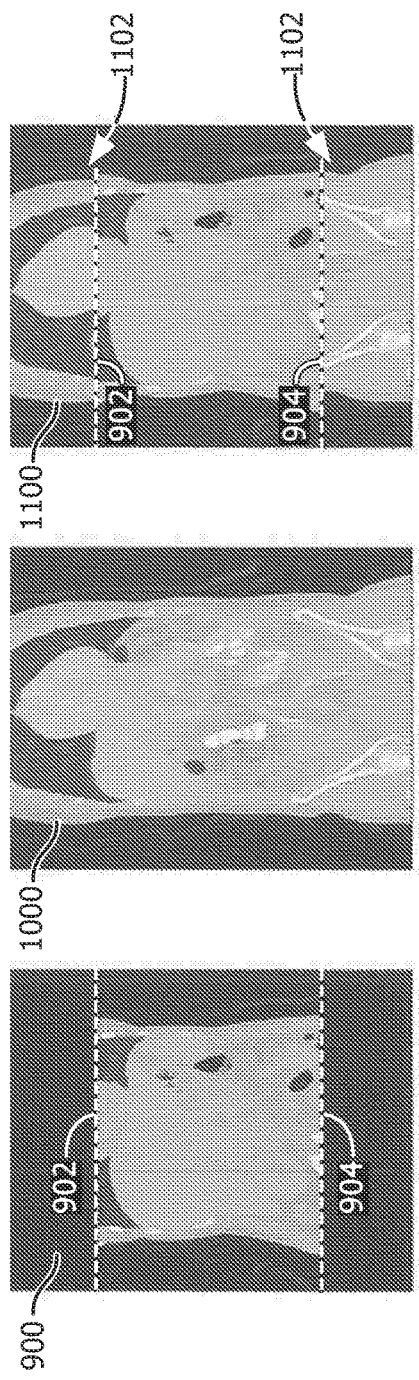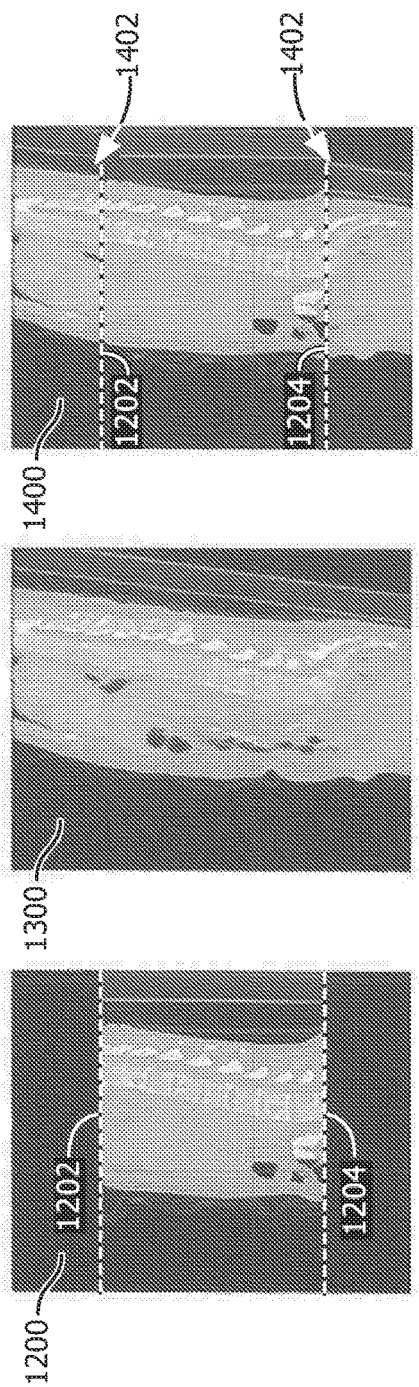

IMAGE DATA Z-AXIS COVERAGE EXTENSION FOR TISSUE DOSE ESTIMATION

CROSS REFERENCE TO RELATED APPLICATIONS

This application is the U.S. National Phase application under 35 U.S.C. §371 of International Application No. PCT/IB2014/064425, filed Sep. 11, 2014, published as WO 20115/044817 on Apr. 2, 2015, which claims the benefit of U.S. Provisional Patent Application No. 61/883,566 filed Sep. 27, 2013. These applications are hereby incorporated by reference herein.

The following generally relates to image data processing and more particularly to extending the volume of acquired image data for calculation of a dose of scanned tissue and is described with particular application to computed tomography (CT); however, the following also contemplates other apparatuses that emit ionizing radiation such as a X-ray imager, a radiation therapy device, and/or other apparatus.

A CT scanner generally includes an x-ray tube mounted on a rotatable gantry opposite a detector array located across an examination region. The rotatable gantry, and hence the x-ray tube, rotates around the examination region, and the x-ray tube emits ionizing radiation that traverses the examination region and a portion of a subject therein. The detector array detects the radiation and generates projection data indicative thereof. A reconstructor reconstructs the projection data, generating volumetric image data, which can be processed to generate one or more images.

The emitted ionizing radiation, unfortunately, may cause damage to organ cells of the scanned subject. Ionizing radiation absorbed by a scanned subject has been referred to as "dose." An effective dose has been computed as a weighted sum of specific organ doses to the subject due to the ionizing radiation, and it takes into account both the type of radiation and the nature of each organ being irradiated. For instance, the effective dose computation takes into account radio-sensitive organs like the lungs, intestines, or the reproductive system by applying higher weights for these organs relative to other organs.

Organ-specific dose has been computed by dividing the total deposited energy by the mass of the organ. Scatter radiation (radiation outside the field of view (FOV)) may also contribute to the dose. That is, radiation does not stop at the boundary of the imaged FOV, and organs beyond the reconstructed FOV are also irradiated due to scatter. The dose outside of the FOV should also be considered in the computation of the effective dose. For this, the deposited energy and mass for the complete organ need to be known, also for parts of the organ that are outside the FOV.

Typically, about ten (10) centimeters (cm) neighboring the reconstructed FOV receive substantial radiation dose. Since the anatomical information outside the reconstructed FOV is not available, the mass and density of the organs in this region need to be estimated. One approach to estimate the region outside the FOV is to just repeat the first and last slices of the image data for up to 10 cm. Unfortunately, this approach does not reflect the true geometry of the irradiated anatomy, potentially leading to an inaccurate dose estimate.

Aspects described herein address the above-referenced problems and others.

The following describes an approach for extending a field of view of image data of a subject for estimating a dose of the subject from a scan. The approach includes identifying a portion of previously acquired image data and/or an anatomical atlas image data outside the field of view through imaged data registration and extending the field of view with the identified image data.

In one aspect, a method for extending initial image data of a subject for dose estimation includes obtaining first image data of the subject for dose calculation, wherein the first image data has a first field of view. The method further includes obtaining second image data for extending the field of view of the first image data. The second image data has a second field of view that is larger than the first field of view. The method further includes extending the first field of view based on the second image data, producing extended image data.

In another aspect, an image data coverage extender includes a data retriever that retrieves image data for extending a first field of view of initial image data of a subject. The retrieved image data has a second field of view that is larger than the first field of view. The image data coverage extender further includes a registration component that registers the retrieved image data to the initial image data. The image data coverage extender further includes a data extractor that extracts a sub-portion of the second image data that is outside the first field of view. The image data coverage extender further includes a data combiner that combines the initial image data and the extracted sub-portion, generating the extended image data, and outputs the extended image data.

In another aspect, a computer readable storage medium is encoded with computer readable instructions, which, when executed by a processer, causes the processor to: obtain first image data of a subject, wherein the first image data has a first field of view, obtain second image data for extending the field of view of the first image data, wherein the second image data has a second field of view that is larger than the first field of view; determine a sub-portion of the second image data to combine with the first image data to extend the first field of view based on a registration of the second image data to the first image data; extend the first field of view based on the determined sub-portion, producing extended image data, and estimate a dose for the subject based on the extended image data.

The invention may take form in various components and arrangements of components, and in various steps and arrangements of steps. The drawings are only for purposes of illustrating the preferred embodiments and are not to be construed as limiting the invention.

FIG. 1 schematically illustrates an example image data coverage extender in connection with an imaging system and a dose estimator.

FIG. 2 schematically illustrates an example of the image data coverage extender of FIG. 1.

FIG. 3 shows a coronal view of image data to be processed to compute a dose of a scanned subject.

FIG. 4 shows a coronal view of transformed image data of the subject that is used to extend the image data of FIG. 3.

FIG. 5 shows a coronal view of the image data of FIG. 3 extended using the transformed image data of FIG. 4.

FIG. 6 shows a sagittal view of image data to be processed to compute a dose of a scanned subject.

FIG. 7 shows a sagittal view of transformed image data of the subject used to extend the image data of FIG. 6.

FIG. 8 shows a sagittal view of the image data of FIG. 6 extended using the transformed image data of FIG. 7.

FIG. 9 shows a coronal view of image data to be processed to compute a dose of a scanned subject.

FIG. 10 shows a coronal view of transformed atlas image data of the subject that is used to extend the image data of FIG. 9.

FIG. 11 shows a coronal view of the image data of FIG. 9 extended using the transformed atlas image data of FIG. 10.

FIG. 12 shows a sagittal view of image data to be processed to compute a dose of a scanned subject.

FIG. 13 shows a sagittal view of transformed atlas image data of the subject used to extend the image data of FIG. 12.

FIG. 14 shows a sagittal view of the image data of FIG. 12 extended using the transformed atlas image data of FIG. 13.

Figure 1:
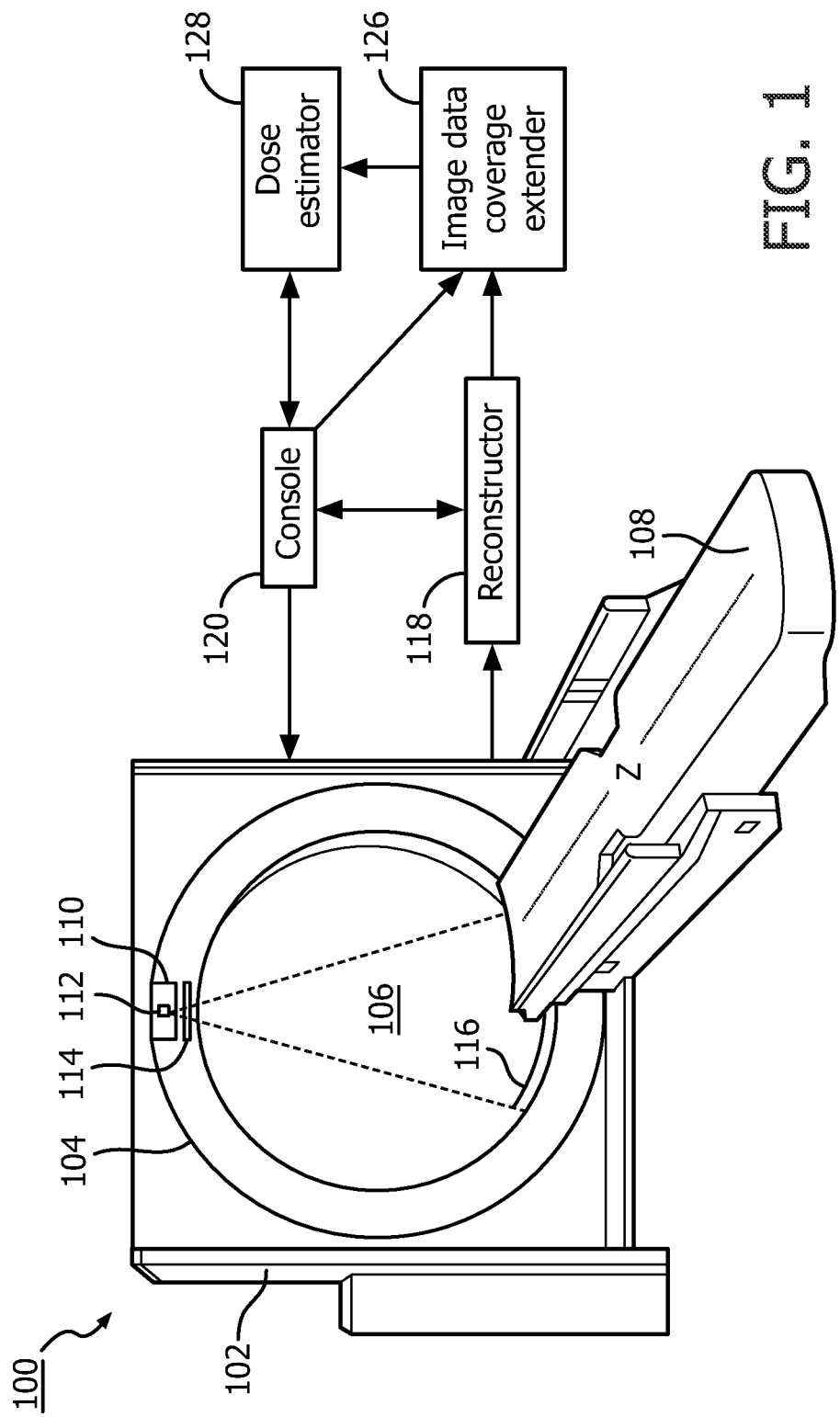

Initially referring to FIG. 1, an imaging system 100 such as a computed tomography (CT) scanner is schematically illustrated. In other embodiments, the imaging system 100 includes another imaging modality that emits ionizing radiation, a therapy treatment device that emits ionizing radiation, and/or other apparatus that emits ionizing radiation.

The imaging system 100 includes a stationary gantry 102 and a rotating gantry 104, which is rotatably supported by the stationary gantry 102. The rotating gantry 104 rotates around an examination region 106 about a longitudinal or z-axis ("Z"). A subject support 108, such as a couch, supports an object or subject in the examination region 106. The subject support 108 can be used to vertically and/or horizontally position the subject or object relative to the imaging system 100 before, during, and/or after scanning.

A radiation source 110, such as an x-ray tube, is supported by and rotates with the rotating gantry 104 around the examination region 106 about the longitudinal or z-axis. The radiation source 110 includes a focal spot 112 and emits x-ray radiation therefrom. A source collimator 114 collimates radiation emitted by the focal spot 112 in a direction of the examination region 106, producing a beam having a pre-determined geometrical shape of interest, such as a fan, a cone, a wedge, or other shaped beam that traverses the examination region 106.

A one or two dimensional detector array 116 subtends an angular arc opposite the examination region 106 relative to the radiation source 110. The detector array 116 detects radiation traversing the examination region 106 and generates a signal (projection data) indicative thereof. A reconstructor 118 reconstructs the signal, generating volumetric image data. A computer serves as an operator console 120 and includes a human readable output device such as a display monitor and an input device such as a keyboard and mouse. Software resident on the console 120 allows the operator to interact with the scanner 100.

An image data coverage extender 126 obtains and extends the volume of the image data along at least the z-axis. For example, where initial image data FOV covers a longitudinal extent from $Z_1$ to $Z_2$, the image data coverage extender 126 can estimate image data for anatomy outside of $Z_1$ to $Z_2$ and combine the estimated image data with the initial image data to produce extended image data from $Z_{1-x1}$, to $Z_{2+x2}$, where x is a non-zero positive real number. By way of example, where the longitudinal extent of the initial image data is $Z_1$ to $Z_2$=80 cm and x1=x2=10 cm, $Z_{1-x1}$ to $Z_{2+x2}$ =100 cm. It is to be understood that this is just an example, and the longitudinal extent can be less than or greater than 80 cm and/or x1 and x2 can be less than or greater than 10 cm. Furthermore, x1 and x2 can be different (e.g., x1=5 and x2=10 cm). Furthermore, x1 and/or x2 can be equal to zero.

As described in greater detail below, the image data coverage extender 126 extends the initial image data with other image data from a previous scan of the same subject, other image data from a previous scan(s) of a different subject(s), for example, a subject with similar physical attributes (e.g., height, weight, age, gender, health state, etc.), anatomical atlas image data, and/or other image data. The extended image data is well suited for dose calculation, for example, since the extended image data extends the initial image data outside of the FOV and thus includes additional tissue outside the FOV that may have been irradiated during the scan. As such, the extended image data may result in a more accurate dose estimation relative to a dose estimation in which only the initial image data is used to estimate the dose.

The image data coverage extender 126 can be implemented via one or more computer processors (e.g., a central processing unit (CPU), a microprocessor, etc.) executing one or more computer executable instructions embedded or encoded on computer readable storage medium, which excludes transitory medium, such as physical memory. At least a sub-portion of the image data coverage extender 126 can be alternatively implemented via the one or more computer processors executing one or more computer executable instructions carried by a carrier wave, signal, and other transitory medium. The image data coverage extender 126 can be part of the console 120 and/or other computing device.

A dose estimator 128 estimates at least an effective dose for the subject based on the extended image data and generates a signal indicative thereof. Examples of dose estimation are described in, but not limited to, U.S. Pat. No. 7,787,669 B2, assigned to Koninklijke Philips Electronics N.V., Eindhoven, N L, filed on Jan. 19, 2004, and entitled "Reconstruction of local patient doses in computed tomography," which is incorporated herein by reference in its entirety, and in U.S. Pat. No. 6,148,272 A, assigned to Koninklijke Philips Electronics N.V., Eindhoven, N L, filed on Jan. 28, 1999, and entitled "System and method for radiation dose calculation within sub-volumes of a monte carlo based particle transport grid," which is incorporated herein by reference in its entirety.

Figure 2:
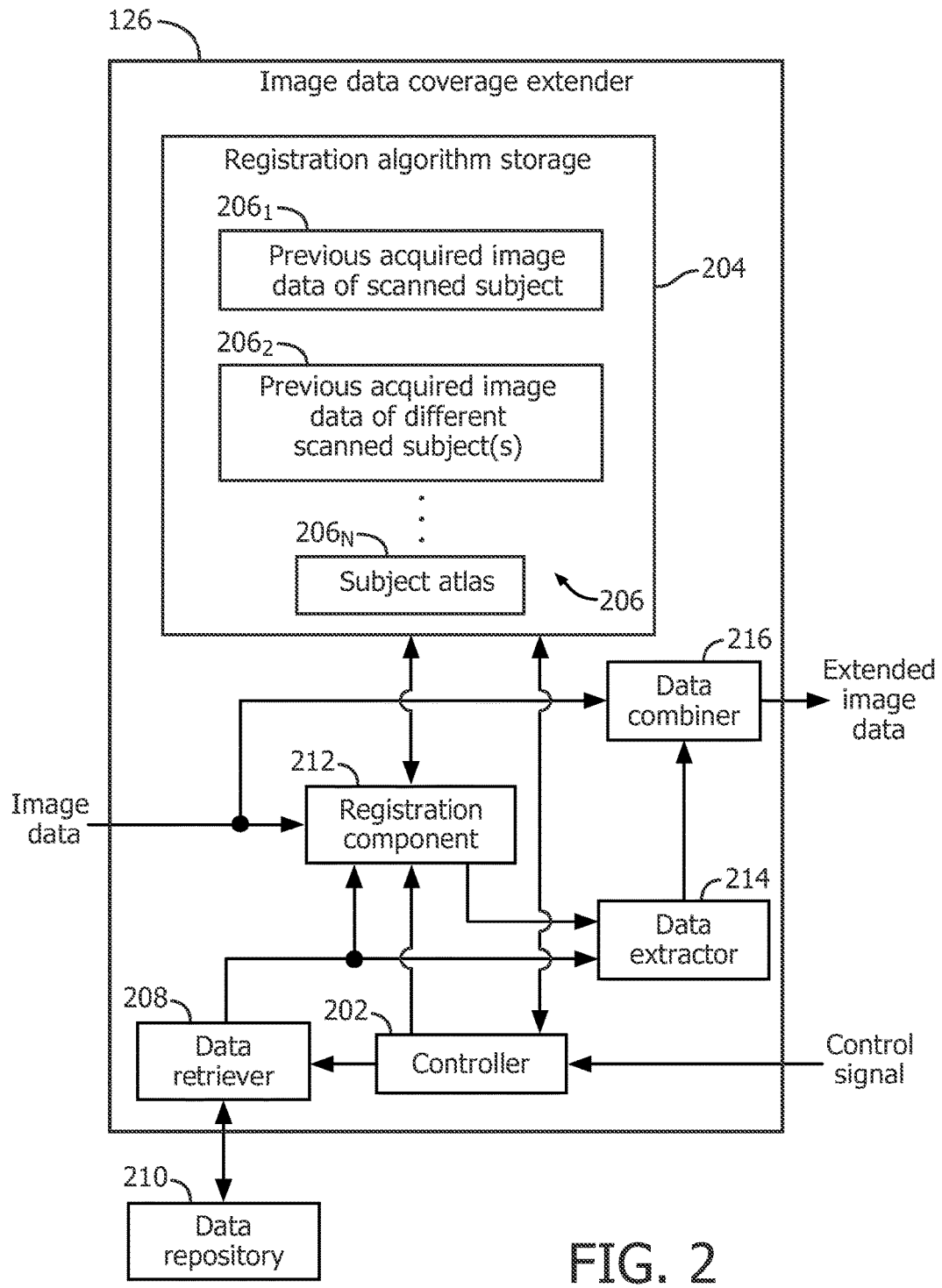

Turning to FIG. 2, an example of the image data coverage extender 126 is schematically illustrated.

The image data coverage extender 126 includes a controller 202, which, in the illustrated example, receives a control signal from the console 120. Where the image data coverage extender 126 is part of a computing device separate from the imaging system 100, the control signal can be generated in response to a user input via an input device of the computing device. The control signal may invoke the controller 202 to obtain initial image data, select a particular registration algorithm to employ which identifies additional image data to extend the initial image data, identify a location of the initial and/or the additional image data, etc.

In the illustrated embodiment, registration algorithm storage 204 stores registration algorithms that identify the additional image data used to extend the initial image data. The registration algorithm storage 204 includes one or more registration algorithms 206. In the illustrated embodiment, the registration algorithm storage 204 includes a previous acquired image data of the scanned subject algorithm $206_1$, a previous acquired image data of a different scanned subject(s) algorithm $206_2$, . . . , and a subject atlas algorithm $206_N$. Other algorithms that facilitate obtaining additional image data to extend the initial image data are also contemplated herein.

The previous acquired image data of the scanned subject algorithm $206_1$ invokes obtaining previously acquired image data of the scanned subject. When this algorithm is employed, the controller 202 invokes a data retriever 208 to retrieve previous acquired image data of the scanned subject, if available. Suitable image data includes image data covering the same or similar anatomical region of the subject as the initial image data, but with a larger FOV and hence further z-axis coverage. The larger z-axis coverage, for example, covers portions of the scanned anatomy that are outside the initial image data FOV that might be exposed to scatter and/or other radiation.

The previous acquired image data of the different scanned subject(s) algorithm $206_2$ invokes obtaining previously acquired image data of a subject(s) different from the scanned subject. When this algorithm is executed, the controller 202 likewise invokes the data retriever 208 to retrieve image data, but for a different scanned subject(s). This data retriever 208 may utilize information about the subject to facilitate retrieving a match such as the particular anatomy scanned, an age, gender, or weight of the subject, and/or other information. Where more than one match is located, the data retriever 208 can apply predetermined rules and/or otherwise select between the matched image data. Likewise, the FOV of this image data must be larger than that of the initial image data.

The subject atlas algorithm $206_N$ invokes obtaining anatomical atlas image data. The anatomical atlas image data, generally, includes generic virtual image data, which mimics a typical (e.g., average) subject with respect to anatomy and spatial relationship, size, and orientation thereof. The anatomical atlas image data can be generic to all subjects or include sub-image data, which provide more specific information based on characteristics such as age, gender, height, weight, etc. If a set of anatomical atlas image data are available, a best fitting atlas can be identified based on a measure of success, e.g., a gray-value difference at the upper and lower image border, i.e., where the FOV is extended. Likewise, the FOV of the atlas must be larger than that of the initial image data.

The data retriever 208 can obtain the previous acquired image data of the scanned subject, the previous acquired image data of the different scanned subject, and/or the subject atlas from a data repository 210 such as a radiology information system (RIS), a hospital information system (HIS), a picture archiving and communication system (PACS), an electronic medical record (EMR), a server, a database, and/or other storage.

A registration component 212 registers the retrieved image data with the initial image data. As discussed herein, the FOV of the retrieved image data must be larger than that of the initial image data. Suitable registrations include an affine registration, an elastic registration, and combinations thereof. For example, in one non-limiting instance, the registration component 212 can apply a global affine registration. This registration can be refined by applying a second pass registration on the first registration, which only considers the regions at the perimeter of the initial image data. With this approach, the first pass registration can be used to facilitate identifying corresponding regions in the initial image data.

Optionally, the registration component 212 extends the affine registration by registering the retrieved image data using a non-parametric approach, which will result in a deformation vector field. To obtain a deformation which also yields information outside the region of the initial image data, the deformation vector field could be extrapolated, and the influence of the non-parametric registration result could fade or diminish with distance from the perimeter of the FOV of the initial image data to the FOV of the retrieved image data, which may result in a stronger impact to the affine registration.

Optionally, the registration component 212 employs a registration algorithm that includes a regularization term, which determines a strength of the non-parametric approach. With this algorithm, the registration component 212 can change or adjust a local impact of the regularization term. An example of such an algorithm is described in Kabus, "Multiple-Material Variational Image Registration," PhD thesis, Universitat zu Lübeck, 2006. In Kabus, the regularization term is dependent on gray-values. The algorithm utilized by the registration component 212 would instead control the regularization term based on a distance to the image boundary, for example, and/or otherwise.

In general, the registration component 212 can utilize any registration approach that yields a global transformation and/or a local transformation, which can be extrapolated for the regions outside the FOV of the initial image data, with the accuracy of the FOV extension depending on the particular registration approach utilized.

A data extractor 214 receives as input the transformed retrieved image data and the initial image data and extracts a sub-portion of the transformed retrieved image data with no correspondence to the obtained image data. That is, the data extractor 214 extracts the sub-portion of the transformed retrieved image data that is outside of the FOV of the initial image data.

A data combiner 216 receives as input the extracted image data and the initial image data and combines the extracted image data and the initial image data, producing extended image data, which includes the initial image data with the addition of the extracted image, which extends the FOV of the initial image data.

The image data coverage extender 126 outputs the extended imaged data. As discussed in connection with FIG. 1, the dose estimator 126 determines the dose for the subject based on the extended image data. The extended image data allows for dose simulations where density values are assumed outside the FOV. The mass and/or dose for an organ can be estimated inside the organs contour. The contours can be obtained by transforming them together with the image date and/or otherwise, e.g., employing segmentation, using the result from the registration as initialization.

Examples showing the extension of initial image data, producing extended image data using the approach describe herein are discussed next.

FIGS. 3-6 show an example in which the retrieved image data is from the same subject. FIG. 3 shows a coronal view of initial image data 300 with first and second boundaries 302 and 304. FIG. 4 shows a coronal view of transformed retrieved image data 400. FIG. 5 shows a coronal view of the extended image data 500, which includes the initial image data 300 of FIG. 3 and a sub-portion 502 of the transformed retrieved image data 400 of FIG. 4 that continues from boundaries 302 and 304 of the initial image data 300 of FIG. 3, extending the FOV of the initial image data 300 of FIG. 3.

FIGS. 6-8 show an example in which the retrieved image data is from the same subject. FIG. 6 shows a sagittal view of initial image data 600 with first and second boundaries 602 and 604. FIG. 7 shows a sagittal view of transformed retrieved image data 700. FIG. 8 shows a sagittal view of the extended image data 800, which includes the initial image data 600 of FIG. 6 and a sub-portion 802 of the transformed retrieved image data 700 of FIG. 7 that continues from boundaries 602 and 604 of the initial image data 600 of FIG. 6, extending the FOV of the initial image data 600 of FIG. 6.

FIGS. 9-11 show an example in which the retrieved image data is from a subject atlas. FIG. 9 shows a coronal view of initial image data 900 with first and second boundaries 902 and 904. FIG. 10 shows a coronal view of transformed retrieved atlas image data 1000. FIG. 11 shows a coronal view of the extended image data 1100, which includes the initial image data 900 of FIG. 9 and a sub-portion 1102 of the transformed retrieved image data 1000 of FIG. 10 that continues from boundaries 902 and 904 of the initial image data 900 of FIG. 9, extending the FOV of the initial image data 900 of FIG. 9.

FIGS. 12-14 show an example in which the retrieved image data is from a subject atlas. FIG. 12 shows a sagittal view of initial image data 1200 with first and second boundaries 1202 and 1204. FIG. 13 shows a sagittal view of transformed retrieved atlas image data 1300. FIG. 14 shows a sagittal view of the extended image data 1400, which includes the initial image data 1200 of FIG. 12 and a sub-portion 1402 of the transformed retrieved atlas image data 1300 of FIG. 13 that continues from boundaries 1202 and 1204 of the initial image data 1200 of FIG. 12, extending the FOV of the initial image data 1200 of FIG. 12.

Figure 15:
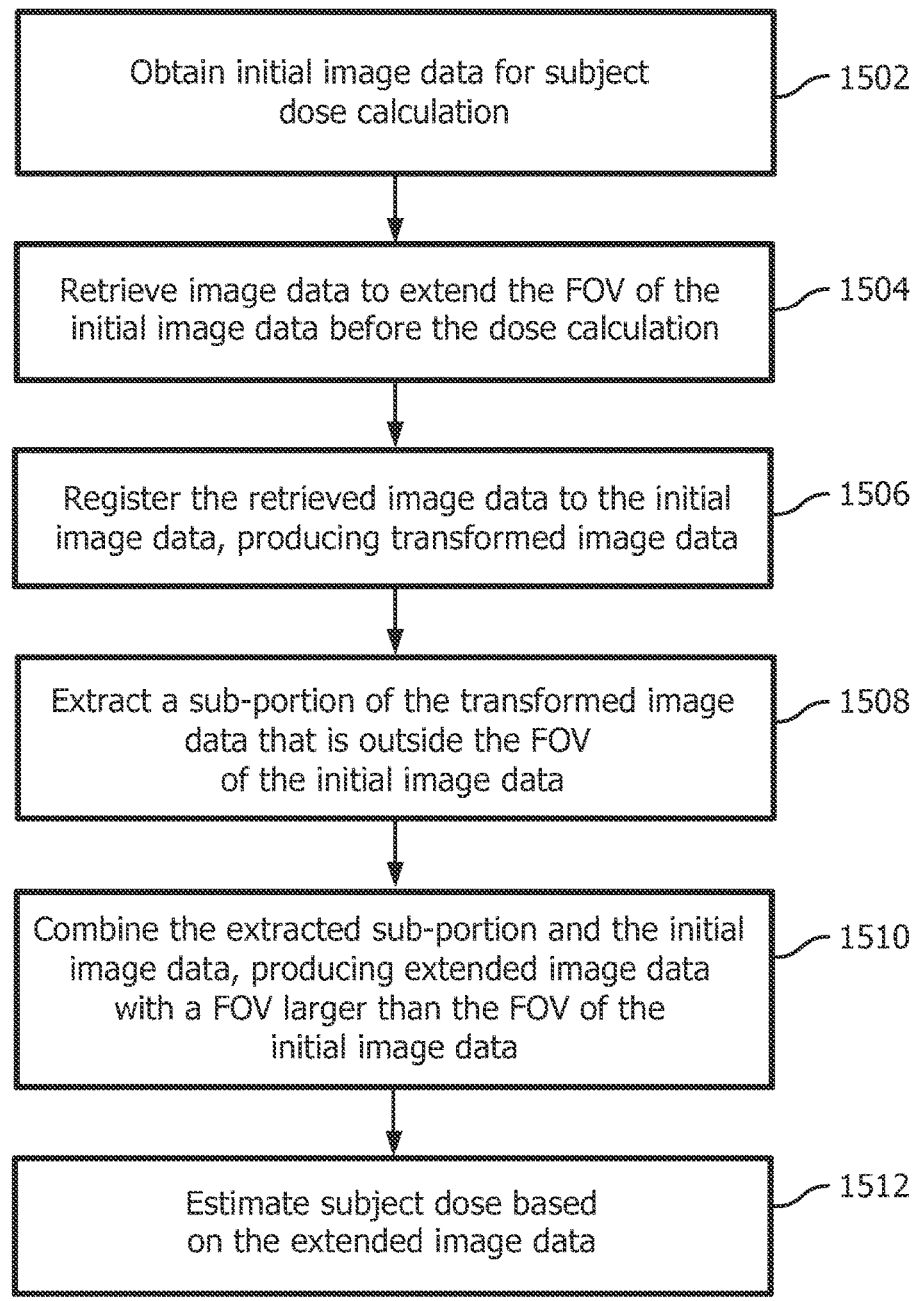
FIG. 15 illustrates an example method for extending the FOV of initial image data for dose estimation of scanned tissue.

FIG. 15 illustrates example method for extending the FOV of initial image data for dose estimation of scanned tissue.

It is to be appreciated that the ordering of the acts of these methods is not limiting. As such, other orderings are contemplated herein. In addition, one or more acts may be omitted and/or one or more additional acts may be included.

At 1502, initial image data is obtained for dose calculation of a scanned subject.

At 1504, additional image data which will be used to extend the FOV of the initial image data before the dose calculation is retrieved.

As discussed herein, such image data can be previously acquired image data of the subject and/or another subject, and/or atlas image data, and include a FOV that is larger than the FOV of the initial image data.

At 1506, the retrieved image is registered to the initial image data, producing transformed imaged data, as described herein and/or otherwise.

At 1508, a sub-portion of the transformed image data outside of the FOV of the initial image data is extracted, as described herein and/or otherwise.

At 1510, the extracted sub-portion and the initial image data are combined, as described herein and/or otherwise, producing extended image data, with a FOV that is larger than the FOV of the initial image data.

At 1512, the extended image data is processed to estimate dose for the scanned subject.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for extending initial image data of a subject for dose estimation, comprising:
   obtaining first X-ray image data of the subject for dose calculation, wherein the first X-ray image data has a first field of view;
   obtaining second X-ray image data for extending the first field of view of the first X-ray image data, wherein the second X-ray image data has a second field of view that is larger than the first field of view;
   registering the second X-ray image data to the first X-ray image data employing a registration algorithm that includes an adjustable regularization term, which determines a strength of the registration and adjusting the regularization term as a function of distance from the first field if view;
   extracting a sub-portion of the second X-ray image data that is outside the first field of view; and
   extending the first field of view based on the second image data by combining the first X-ray image data and the extracted sub-portion, producing extended X-ray image data.

2. The method of claim 1, further comprising:
   estimating a dose for the subject based on the extended X-ray image data.

3. The method of claim 1, wherein the second X-ray image data includes previously acquired X-ray image data of the subject.

4. The method of claim 1, wherein the second X-ray image data includes previously acquired X-ray image data of one or more different subjects.

5. The method of claim 1, wherein the second X-ray image data includes anatomical atlas image data.

6. The method of claim 1, the registering, comprising:
   applying a global affine registration to register the second X-ray image data to the first X-ray image data, producing transformed X-ray image data.

7. The method of claim 6, the registering, comprising:
   performing a second pass registration to the transformed X-ray image data, wherein the second pass registration considers regions at a perimeter of the first image data.

8. The method of claim 1, wherein an impact of the registering gradually diminishes from a perimeter of the first X-ray image data to a perimeter of the second X-ray image data.

9. An image data coverage extender, comprising:
   a data retriever, implemented by a processor, that retrieves image data for extending a first field of view of initial image data of a subject, wherein the retrieved image data has a second field of view that is larger than the first field of view;
   a registration component, implemented by the processor, that registers the retrieved image data to the initial image data, wherein an impact of the registering gradually diminishes from a perimeter of the initial image data to a perimeter of the retrieved image data;
   a data extractor, implemented by the processor, that extracts a sub-portion of the second image data that is outside the first field of view; and
   a data combiner, implemented by the processor, that combines the initial image data and the extracted sub-portion, generating the extended image data, and outputs the extended image data.

10. The image data coverage extender of claim 9, wherein the retrieved image data includes previously acquired image data of the subject.

11. The image data coverage extender of claim 9, wherein the retrieved image data includes previously acquired image data of one or more subjects other than the subject.

12. The image data coverage extender of claim 9, wherein the retrieved image data includes anatomical atlas image data.

13. The image data coverage extender of claim 9, wherein the registration component applies a global affine registration to register the retrieved image data to the initial image data.

14. The image data coverage extender of claim 13, wherein the registration component applies a subsequent registration to refine the global affine registration.

15. The image data coverage extender of claim 9, wherein the registration component employs a registration algorithm including an adjustable regularization term.

16. The image data coverage extender of claim 9, wherein a dose of the subject is determined based on the extended image data.

17. A computer readable storage medium encoded with computer readable instructions, which, when executed by a processer, causes the processor to:

obtain first image data of a subject, wherein the first image data has a first field of view;

obtain second image data for extending the field of view of the first image data, wherein the second image data has a second field of view that is larger than the first field of view;

determine a sub-portion of the second image data to combine with the first image data to extend the first field of view based on a registration of the second image data to the first image data and a second pass registration to the registered first and second image data, wherein the second pass registration considers regions at a perimeter of the first image data; and extend the first field of view based on the determined sub-portion, producing extended image data.

* * * * *